(12) United States Patent
Yanami et al.

(10) Patent No.: US 8,197,754 B2
(45) Date of Patent: Jun. 12, 2012

(54) SAMPLE DISPENSING APPARATUS AND AUTOMATIC ANALYZER INCLUDING THE SAME

(75) Inventors: Hideyuki Yanami, Hitachinaka (JP); Isao Yamazaki, Ryugasaki (JP); Masaaki Hanawa, Hitachinaka (JP); Hitoshi Otake, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/895,040

(22) Filed: Sep. 30, 2010

(65) Prior Publication Data
US 2011/0014085 A1    Jan. 20, 2011

Related U.S. Application Data

(63) Continuation of application No. 10/780,743, filed on Feb. 19, 2004, now Pat. No. 7,824,915.

(30) Foreign Application Priority Data

Mar. 19, 2003    (JP) .................................. 2003-74751

(51) Int. Cl.
*G01N 35/10* (2006.01)
*G01N 1/14* (2006.01)

(52) U.S. Cl. ............. 422/64; 422/63; 422/67; 422/501; 422/517; 422/518; 436/43; 436/45; 436/180; 436/49; 73/863.32; 73/864.21

(58) Field of Classification Search .................... None
See application file for complete search history.

(56) References Cited

U.S. PATENT DOCUMENTS

| | | | | |
|---|---|---|---|---|
| 4,276,260 A | * | 6/1981 | Drbal et al. | .................... 422/510 |
| 4,451,433 A | * | 5/1984 | Yamashita et al. | .............. 422/63 |
| 5,445,037 A | | 8/1995 | Itoh | |
| 5,540,081 A | | 7/1996 | Takeda et al. | |
| 5,677,188 A | | 10/1997 | Mitsumaki et al. | |
| 5,717,148 A | | 2/1998 | Ely et al. | |
| 5,762,872 A | | 6/1998 | Buhler et al. | |
| 5,885,530 A | | 3/1999 | Babson et al. | |
| 7,015,042 B2 | | 3/2006 | Devlin, Sr. | |
| 2003/0049171 A1 | | 3/2003 | Tamura et al. | |
| 2003/0213313 A1 | | 11/2003 | Katagi | |

FOREIGN PATENT DOCUMENTS

| | | |
|---|---|---|
| EP | 0 250-671 | 7/1986 |
| EP | 0 601 213 | 10/1992 |
| JP | 3-140869 | 6/1991 |
| JP | 2001-66316 | 3/2001 |
| WO | 03/012454 | 7/2002 |

* cited by examiner

*Primary Examiner* — P. Kathryn Wright
(74) *Attorney, Agent, or Firm* — Mattingly & Malur, PC

(57) ABSTRACT

The invention provides a small-sized automatic analyzer being compact, enabling a large number of analysis items to be carried out, and having a high processing speed. The automatic analyzer is particularly suitably applied to a medical analyzer used for qualitative/quantitative analysis of living body samples, such as urine and blood. A plurality of sample dispensing mechanism s capable of being operated independently of each other are provided to suck a sample from any one of a plurality of sample suction positions and to discharge the sucked sample to any one of a plurality of positions on a reaction disk. The automatic analyzer having a high processing capability can be thus realized without increasing the system size.

3 Claims, 5 Drawing Sheets

SAMPLE DISPENSING APPARATUS AND AUTOMATIC ANALYZER INCLUDING THE SAME

This is a continuation application of U.S. application Ser. No. 10/780,743, filed Feb. 19, 2004, now allowed, which claims priority to JP 2003-74751, filed Mar. 19, 2003, the contents of which are hereby incorporated by reference into this application.

BACKGROUND OF THE INVENTION

1. Field of the Invention

The present invention relates to a sample dispensing apparatus for use in an analyzer in which a sample and a reagent are mixed with each other to carry out qualitative/quantitative analysis of a particular ingredient in the sample, and to an automatic analyzer including the sample dispensing apparatus. More particularly, the present invention relates to a sample dispensing apparatus with a high sampling (pipetting) capability per hour, and to an automatic analyzer including the sample dispensing apparatus.

2. Description of the Related Art

Taking as an example a medical automatic analyzer used for analyzing particular ingredients in living body samples, such as blood and urine, the medical automatic analyzer is essential for carrying out analysis with high efficiency in, e.g., large-, medium- and small-scaled hospitals handling a large number of patients, and a clinic center carrying out analysis under contract with those hospitals or doctor's offices.

In that type of automatic analyzer, it is demanded that the analyzer is more compact, is able to perform more kinds of analysis, and has a higher processing speed. To satisfy those demands, various kinds of automatic analyzers have been proposed so far.

One measure for increasing the processing speed is to increase a sampling speed. Patent Reference 1, JP,A 3-140869, discloses an automatic chemical analyzer including a sample dispensing mechanism wherein two sampling nozzles are provided such that the sampling nozzles are able to carry out sampling from one sample container to two reaction cuvettes at different timings.

Also, Patent Reference 2, JP,A 2001-66316, discloses a sample dispensing apparatus wherein one sampling arm is provided with a plurality of sampling nozzles, and the sampling nozzles can be controlled to discharge samples independently of each other.

SUMMARY OF THE INVENTION

With the method disclosed in Patent Reference 1, two dispensing probes are able to perform the dispensing operations at different timings, and therefore 1200 tests/hour can be processed with the operation equivalent to that required for processing 600 tests/hour in usual cases. According to the embodiment described in Patent Reference 1, however, the two dispensing probes are supported by one probe shaft and they cannot perform the dispensing operations independently of each other. It is thus considered that the two dispensing probes cannot be disposed on the same plane of rotation from the structural point of view and the dispensing operations of the two dispensing probes must be synchronized with each other.

Also, with the method disclosed in Patent Reference 2, because two dispensing probes are provided on one dispensing arm, it is considered that the two dispensing probes cannot perform the dispensing operations at free different timings similarly to the method disclosed in Patent Reference 1.

Accordingly, it is an object of the present invention to provide a sample dispensing apparatus and an automatic analyzer including the sample dispensing apparatus, which has a plurality of dispensing probes capable of performing the dispensing operations independently of each other, and can increase a dispensing speed while realizing the dispensing operations at flexible timings.

The sample dispensing apparatus of the present invention is suitably employed in a medical automatic analyzer, but it is as a matter of course that the sample dispensing apparatus is also applicable to analyzers for organic/inorganic samples, etc.

To achieve the above object, the present invention is constituted as follows.

In a sample dispensing apparatus comprising a sample container loading mechanism capable of loading a plurality of sample containers each containing a sample to be analyzed and including a mechanism capable of changing arrangement of the plurality of sample containers; a reaction cuvette loading mechanism capable of loading a plurality of reaction cuvettes in each of which the sample to be analyzed and a reagent are mixed with each other, and including a mechanism capable of changing arrangement of the plurality of the reaction cuvettes; and a sample dispensing mechanism for sucking the sample from the sample container and discharging the sucked sample into the reaction cuvette, the sample dispensing apparatus includes a plurality of sample dispensing mechanisms including nozzles for sucking and discharging the sample, the plurality of nozzles being vertically movable to suck and discharge the sample independently of each other, and mechanisms capable of moving the nozzles between the sample container and the reaction cuvette independently of each other.

The sample container loading mechanism may be in any desired form so long as it is able to move the position of each sample container. For example, the sample container loading mechanism may include a sample disk capable of loading the plurality of sample containers arranged thereon along a periphery of the disk. While the expression "sample disk" is used, the sample disk is not always limited to a circular disk. Stated another way, in the case of employing a circular disk, the expression "along a periphery of the disk" can be regarded as meaning "along a circumference of the disk".

As an alternative form of the sample container loading mechanism, a rack capable of loading one or more sample containers may be used and moved to convey each sample container.

The reaction cuvette loading mechanism can also be embodied in various forms. More specifically, the reaction cuvette loading mechanism may be in the form of a reaction disk, or may have a structure capable of linearly moving the reaction cuvettes.

DESCRIPTION OF THE PREFERRED EMBODIMENTS

Figure 1:
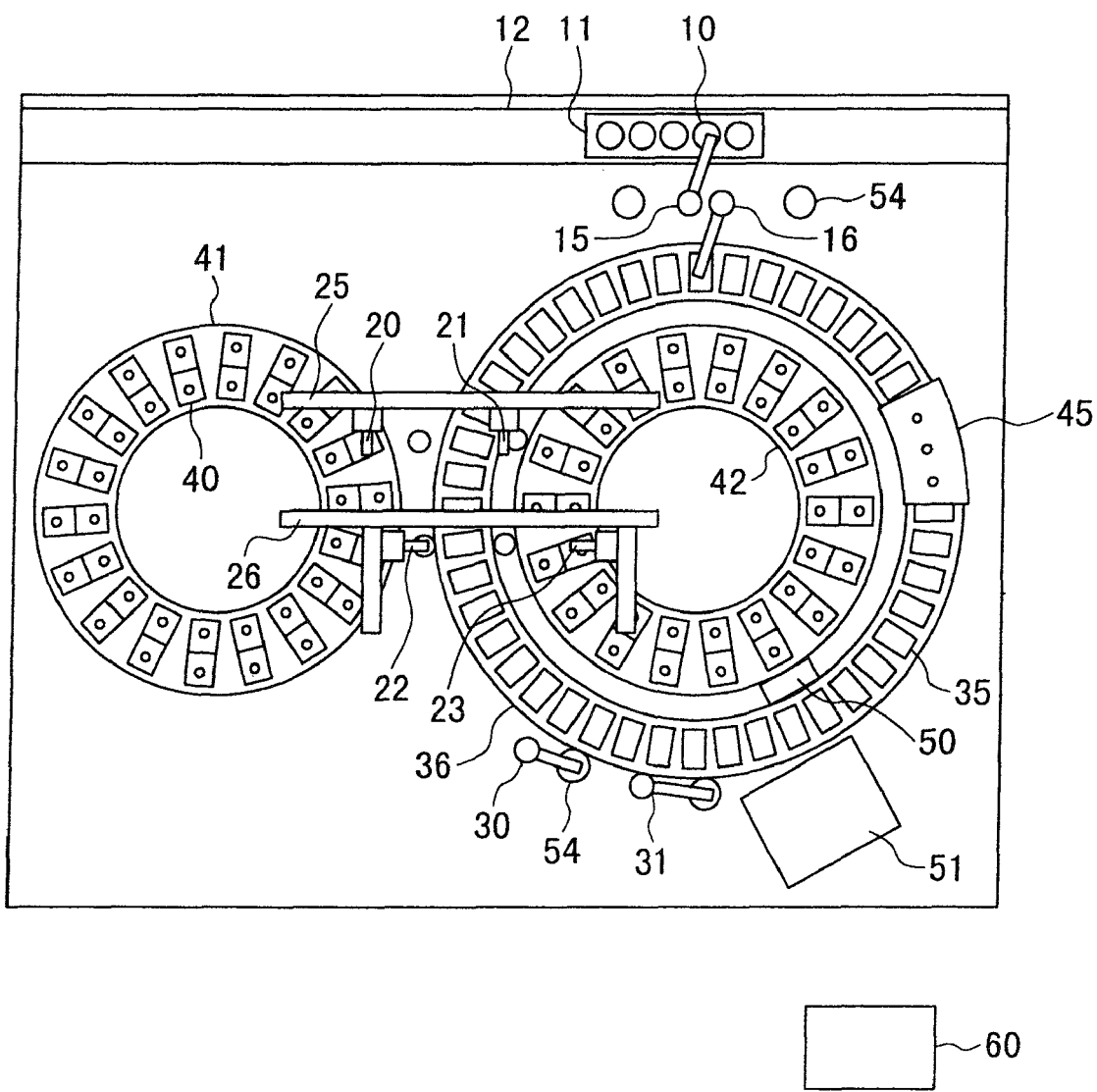
FIG. 1 is a plan view of an automatic analyzer to which the present invention is applied.

In the present invention, each of the sample dispensing mechanisms repeats operations of sucking the sample and discharging the sucked sample into the reaction cuvette. The provision of the plurality of nozzles enables those operations to be performed such that while one sample dispensing mechanism discharges the sample into the reaction cuvette on the reaction disk after sucking the sample, the other nozzle sucks the sample. Accordingly, the standby time of the nozzle until it starts the suction of the sample can be cut down and high-speed processing can be realized.

Because a plurality of sample dispensing mechanisms are able to carry out the dispensing operations independently of each other, the sample can be sucked from the sample container at a shorter interval. Correspondingly, the time allowed for the sample container to move to a sample suction position is shortened and a difficulty rises in moving the sample container to one predetermined location in time. This acts as a factor reducing the processing capability. However, a reduction of the processing capability can be avoided by constructing each of the sample dispensing mechanisms to be able to suck the sample from plural sample suction positions.

The sample dispensing apparatus includes the moving mechanism capable of reciprocating the nozzle between the sample suction position and the reaction disk. A path along which the sample dispensing mechanism moves may be linear or curved. To enable the sample dispensing mechanisms to operate independently of each other, however, some means is required for avoiding the sample dispensing mechanisms from interfering with each other. For example, when the sample dispensing mechanisms are operated in the same plane, escape positions are provided on the paths of movements of the sample dispensing mechanisms so that one of the sample dispensing mechanisms will not restrict the operation of the other sample dispensing mechanism between the sample suction position and the reaction disk, or the sample dispensing mechanisms are disposed such that the paths of their movements are surely kept from interfering with each other. Alternatively, moving parts of the sample dispensing mechanisms are disposed in a vertically spaced relation to be kept out of interference between them. As an alternative, it is also possible to provide rotary shafts each positioned at middle between the sample suction position and the reaction disk, and to move the plural sample dispensing mechanisms to the sample suction position or the reaction disk by utilizing the respective rotary shafts. When the sample dispensing mechanisms are moved by utilizing the rotary shafts, each of the sample dispensing mechanisms may be provided with any other suitable moving means so that the sample dispensing mechanism can be moved to desired one of plural sample suction positions and desired one of plural positions on the reaction disk.

The nozzle may have a liquid level detecting function for confirming whether the least necessary amount of the sample is present in the sample container or not, in order that the sample can be positively sucked with the aid of the liquid level detecting function. In the sample dispensing apparatus including the plurality of sample dispensing mechanisms, at the time when it is determined in any one of the sample dispensing mechanisms that the sample container does not contain the sample in amount not sufficient to ensure positive sucking of the sample, another sample dispensing mechanism that has been scheduled to suck the sample from the same sample container can be controlled in accordance with the determination result so as to stop sucking of the sample from the same sample container and to make a shift of the sucking operation to the next sample container. As a result, the unnecessary operation of the sample dispensing mechanism can be reduced.

The nozzle may also have a clogging detecting function for confirming whether any factor causing clogging in a flow passage of the nozzle is present in the sample container or not. In the sample dispensing apparatus including the plurality of sample dispensing mechanisms, at the time when it is determined in any one of the sample dispensing mechanisms that any factor causing clogging is present in the sample container, another sample dispensing mechanism that has been scheduled to suck the sample from the same sample container can be controlled in accordance with the determination result so as to stop sucking of the sample from the same sample container and to make a shift of the sucking operation to the next sample container. As a result, the unnecessary operation of the sample dispensing mechanism can be reduced.

Further, even in the case of one of the nozzles having failed to operate due to any abnormality, because the sample dispensing apparatus includes the plurality of sample dispensing mechanisms capable of operating independently of each other, the analyzing operation can be continued by using the sample dispensing mechanism operating normally unless operations of all the sample dispensing mechanisms are disabled upon abnormalities at the same time.

In other words, if at least one of the plurality of nozzles is able to normally operate, the analysis can be performed by operating only the operable one of the plurality of sample dispensing mechanisms.

In sample dispensing, for the purpose of avoiding thinning of the sample in the flow passage, the sample is also sucked as a dummy in addition the amount of the sample actually pipetted into the reaction cuvette. The dummy is finally discharged and discarded into a washing tank. While the provision of the plurality of sample dispensing mechanisms increases the processing capability, it is sometimes important to carry out all of the analysis items requested for the sample with priority over a reduction of the processing capability, for example, when the amount of the sample is very small such as a sample taken from an infant. In that case, the sample dispensing operation is controlled in accordance with information obtained from the sample container so as to carry out all of the requested analysis items even for the sample in a very small amount by operating only a particular one of the sample dispensing mechanisms to suck and discharge the sample instead of employing all of the sample dispensing mechanisms. When the sample dispensing operation is carried out in different ways depending on the type of the sample contained in the sample container as mentioned above, whether to make the function of selectively operating the sample dispensing mechanisms effective or not can be set, for example, from an operating screen on a display. As a result, it is possible to provide the sample dispensing apparatus having a higher value added.

The larger the number of nozzles, the higher is the processing speed. However, the increased number of nozzles requires a larger space and a more complicated structure because of the problems that escape positions must be prepared for the respective sample dispensing mechanisms to avoid interference between them, and that the number of reagent dispensing mechanisms for discharging reagents into the reaction cuvettes, into which the samples have been discharged, must also be increased. Thus, the number of nozzles is desirably selected, as appropriate, depending on the required processing capability, etc.

Figure 2:
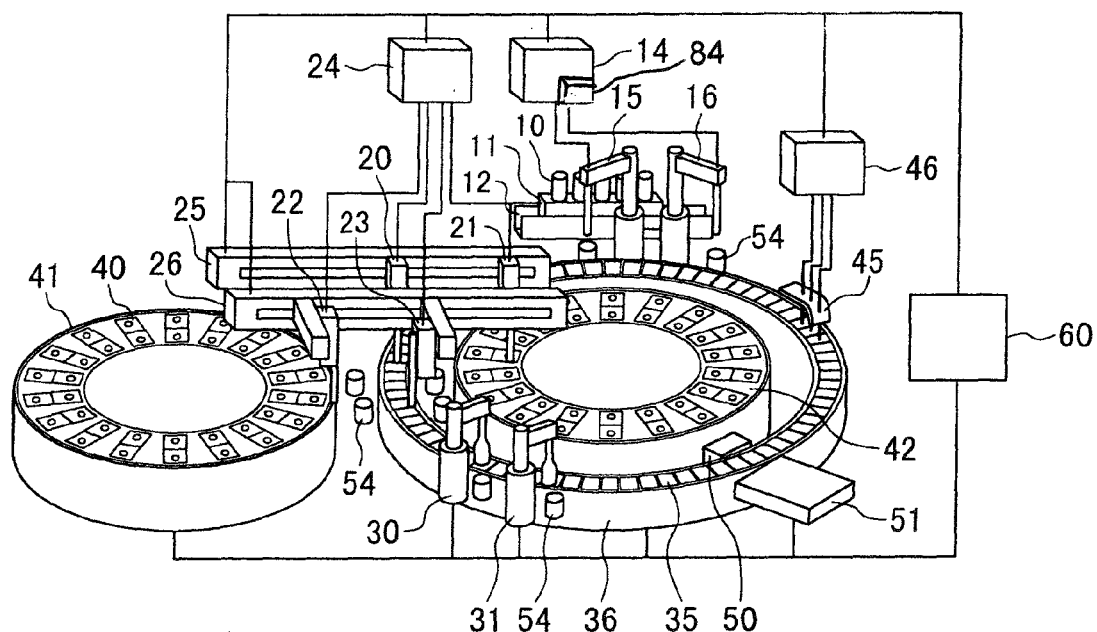
FIG. 2 is a perspective view of the automatic analyzer to which the present invention is applied.

Embodiments of the present invention will be described below with reference to the drawings. FIGS. 1 and 2 are respectively a plan view and a perspective view of one embodiment according to the present invention. Reaction cuvettes 35 are arranged on a reaction disk 36 along its circumference. A reagent disk 42 is disposed inside the reaction disk 36, and a reagent disk 41 is disposed outside the reaction disk 36. A plurality of reagent containers 40 are loadable on each of the reagent disks 41, 42 along its circumference. One reagent container 40 contains two kinds of reagents. A conveyer mechanism 12 for moving a rack 11 with sample containers 10 loaded thereon is installed near the reaction disk 36. Rails 25, 26 are laid to extend between both the reagent disks 41 and 42 at a level above them. Reagent probes 20, 21 are disposed on the rail 25 to be movable not only in the direction parallel to the rail 25, but also in the vertical direction. Reagent probes 22, 23 are disposed on the rail 26 to be movable in the 3-axis directions with respect to the rail 26. The reagent probes 20, 21, 22 and 23 are connected to a reagent pump 24. Between the reaction disk 36 and the conveyer mechanism 12, sample probes 15, 16 are disposed to be rotatable in respective planes and movable in the vertical direction.

The sample probes 15, 16 are each moved along a circular arc about a rotary shaft to alternately dispense a sample from the sample container into the reaction cuvettes. The sample probes 15, 16 include mechanisms capable of changing the probe heights, and perform dispensing operations at the timings and the probe heights both properly adjusted in accordance with a preset program so that the movements of both the sample probes will not interfere with each other.

Figure 3:
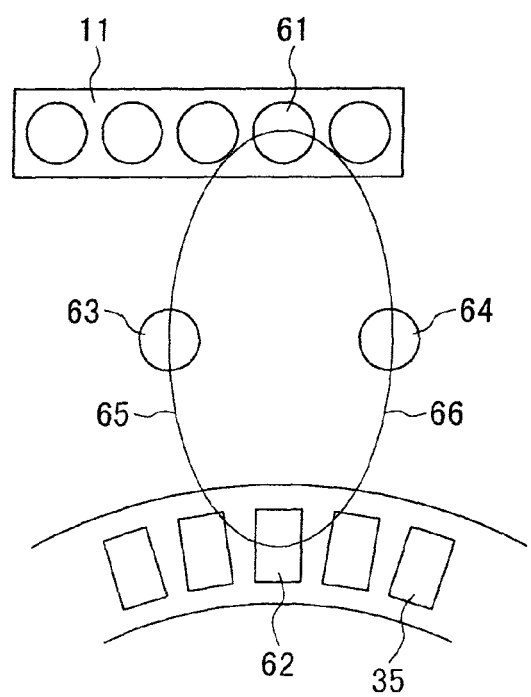
FIG. 3 is an explanatory view showing operations of sample dispensing mechanisms (sample probes) according to another embodiment of the present invention, looking from above.
Figure 4:
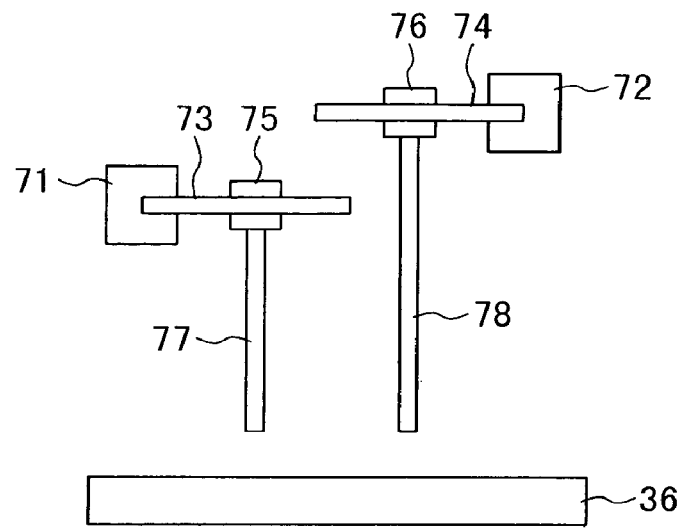
FIG. 4 is an explanatory view showing operations of the sample dispensing mechanisms(sample probes) in the present invention, looking from side.
Figure 5:
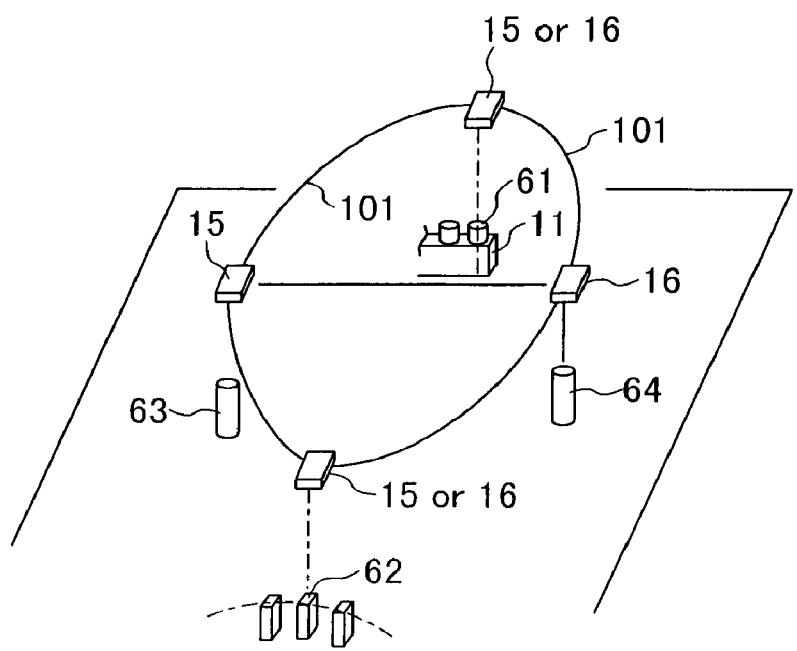
FIG. 5 is a schematic perspective view of a sample dispensing mechanism in the present invention.

A construction of a sample dispensing mechanism according to another embodiment will be described below with reference to FIGS. 3, 4 and 5. FIG. 3 shows, from above an analyzer, the paths along which the sample probes move, FIG. 4 shows structures of the sample probes from the front of the analyzer, and FIG. 5 is a perspective view showing a mechanism for moving the sample probes. The sample probes 15, 16 are each moved between one sample container 61 placed on the rack 11 and located in a position where a sample is to be sucked by the sample probe and one of the reaction cuvettes 35 located in a position 62 where a sample is to be discharged from the sample probe. The sample probe 15 is movable among three points, i.e., the sample container 61, the sample discharge position 62, and a washing position 63. Numeral 65 denotes the path along which the sample probe 15 moves. On the other hand, the sample probe 16 is movable among three points, i.e., the sample container 61, the sample discharge position 62, and a washing position 64. Numeral 66 denotes the path along which the sample probe 16 moves.

The sample probe 15 is movable along a rail 71 by a drive source (not shown) in the back-and-forth direction between the sample container 61 and the sample discharge position 62, while it is movable along a rail 73 by a drive source (not shown) in the left-and-right direction between the washing position 63 and the sample container 61 or the sample discharge position 62. The operation of moving the sample probe 15 in the back-and-forth direction and the operation of moving the sample probe 15 in the left-and-right direction are performed such that one of those operations follows the other. As a result, a sample probe head 75 is movable in a plane constituted by both the rails 71, 73, and a nozzle 77 having a vertical moving mechanism enables the sample probe head 75 to move in a three-dimensional space.

Similarly, the sample probe 16 is movable along a rail 72 by a drive source (not shown) in the back-and-forth direction between the sample container 61 and the sample discharge position 62, while it is movable along a rail 74 by a drive source (not shown) in the left-and-right direction between the washing position 64 and the sample container 61 or the sample discharge position 62. The operation of moving the sample probe 16 in the back-and-forth direction and the operation of moving the sample probe 16 in the left-and-right direction are performed such that one of those operations follows the other. As a result, a sample probe head 76 is movable in a plane constituted by both the rails 72, 74, and a nozzle 78 having a vertical moving mechanism enables the sample probe 76 head to move in a three-dimensional space.

Also, each of the sample probes 15, 16 has a liquid level detecting function and a clogging detecting function. Further, the sample probes 15, 16 are connected to a sample pump 14, and operations of the sample probes 15, 16 are controlled by drive systems independent from each other.

Around the reaction disk 36, there are arranged mixing units 30, 31, a light source 50, an optical detector 51, and a cuvette washing mechanism 45. The cuvette washing mechanism 45 is connected to a washing pump 46. Washing ports 54 are disposed within respective areas where the sample probes 15, 16, the reagent probes 20, 21, 22 and 23, and the mixing units 30, 31 are movable. A sample pump 14, the reagent pump 24, the washing pump 46, the optical detector 51, the reaction disk 36, the reagent disk 41, the reagent probes 20, 21, 22 and 23, and the sample probes 15, 16 are each connected to a controller 60.

The analysis sequence of the analyzer having the above-mentioned construction will be described below.

A sample to be analyzed, such as blood, is put in the sample container 10, and the sample container 10 is placed on the rack 11 and then conveyed by the conveyer mechanism 12.

The sample in the sample container 61 is sucked by the sample probe 15 or 16 and then pipetted into the sample discharge position 62.

The sample probe 15 is initially positioned in the washing position 63, and the sample probe 16 is initially positioned in the washing position 64.

The sample probe 15 is moved on the rails 71 and 73 to the sample suction position (i.e., the position of the sample container 61) where the sample probe head 75 is descended toward the sample container 61 from above it. After sucking the sample, the sample probe head 75 ascends and the sample probe 15 is moved to the sample discharge position (i.e., the position of the sample discharge position 62) where the sucked sample is discharged into the sample discharge position 62. Similarly, the sample probe 16 is moved on the rails 72 and 74 to the sample suction position where the sample probe head 76 is descended toward the sample container 61 from above it. After sucking the sample, the sample probe head 76 ascends and the sample probe 16 is moved to the sample discharge position where the sucked sample is discharged into the sample discharge position 62.

Figure 6:
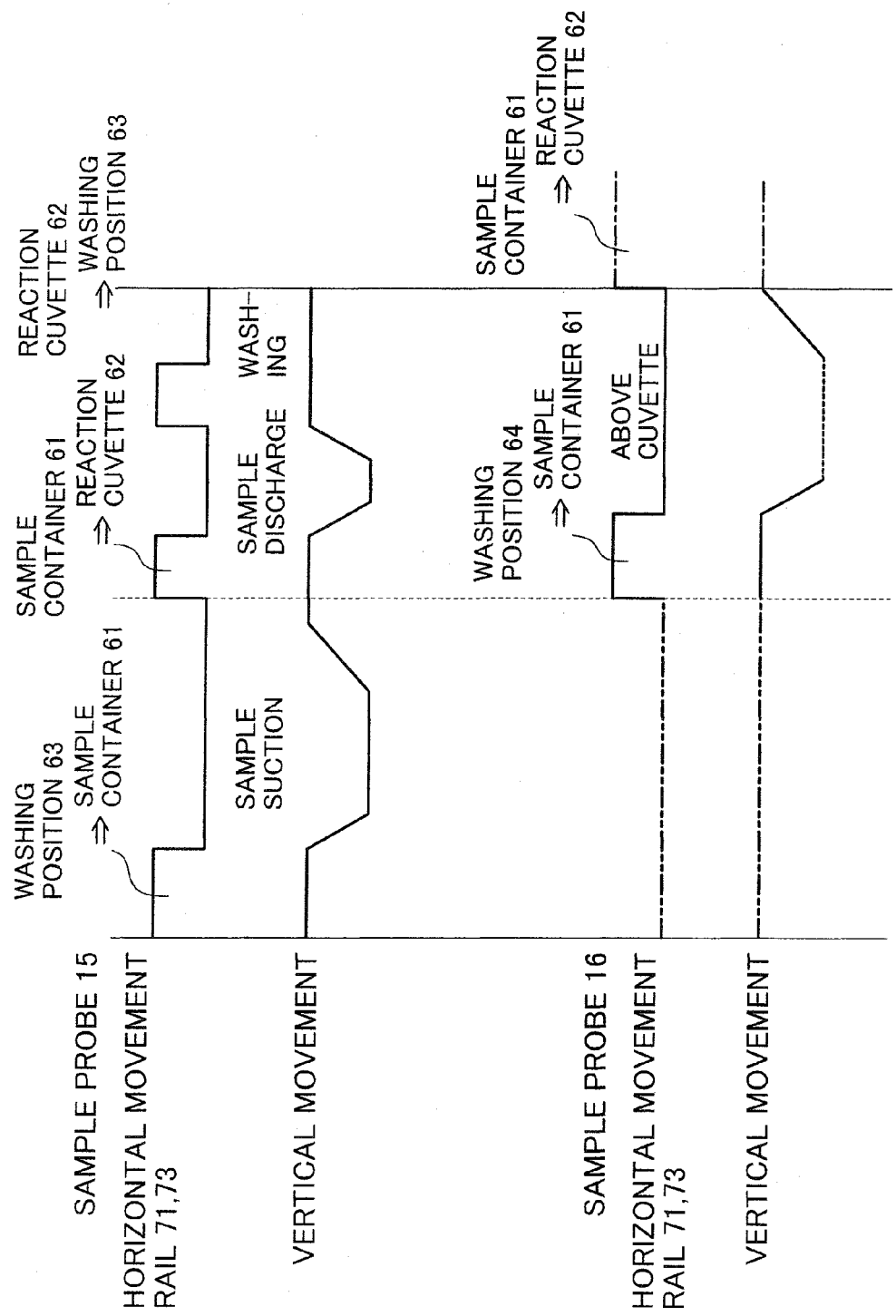
FIG. 6 is a time chart showing sampling timings.
Figure 7:
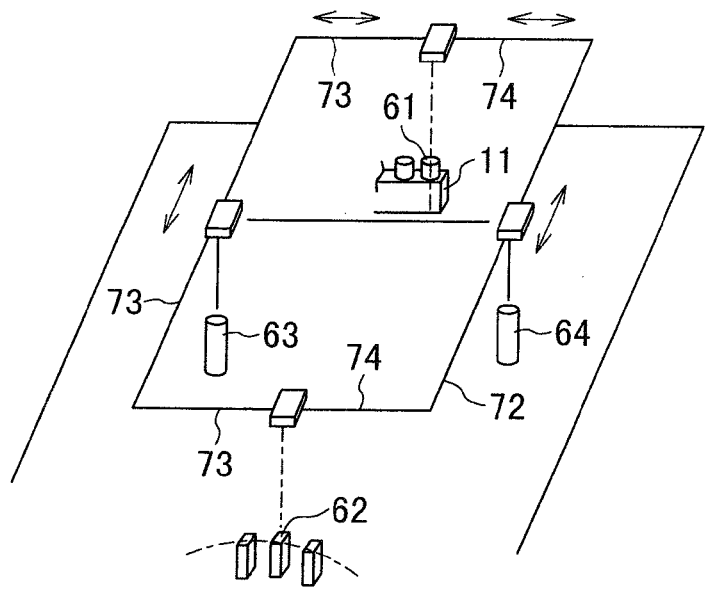
FIG. 7 shows still another embodiment of the present invention.
Figure 8:
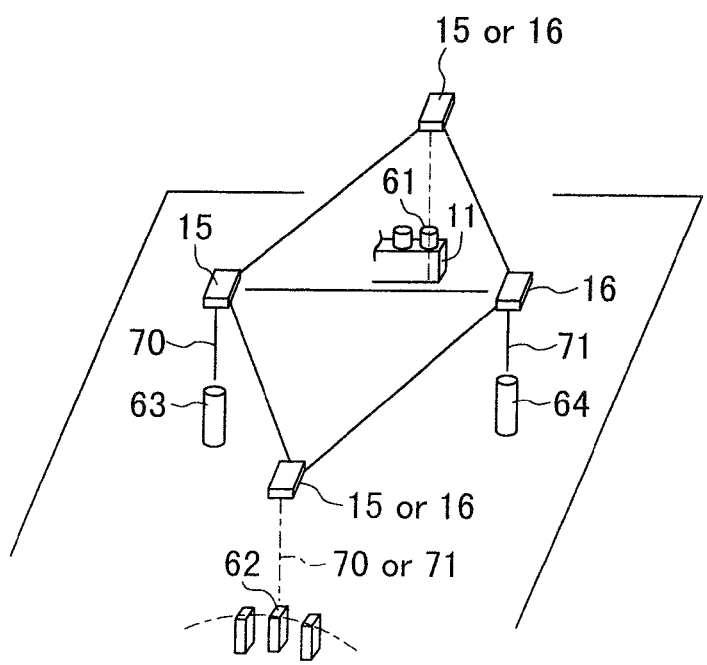
FIG. 8 shows still another embodiment of the present invention.

As seen from a time chart shown in FIG. 6, when sucking the sample by the sample probe 15, for example, the sample probe 15 is moved to the sample suction position where the sample is sucked from the sample container 61. Then, the sample probe 15 is moved to the sample discharge position where the sucked sample is discharged into the sample discharge position 62. In parallel to the movement of the sample probe 15 to the sample discharge position 62, the sample probe 16 starts moving from the washing position 64 toward the sample container 61. At this time, to prevent the sample probes 15, 16 from colliding with each other, the sample probe 15 is moved toward the sample discharge position 62 via the washing position 63. Likewise, after sucking the sample from the sample container 61, the sample probe 16 is moved toward the sample discharge position 62 via the washing position 64 for discharge of the sucked sample. As a result, the time interval of sucking the sample from the sample container can be shortened. For carrying out the operation in accordance with the time chart shown in FIG. 6, it is required to construct a mechanism such that the two sample probes do not cross each other in their movements. FIGS. 7 and 8 show other mechanisms to realize the intended operation than that shown in FIG. 5.

The difference between FIGS. 7 and 5 resides in that a curved rail 101 following the movement paths of the sample probes is employed in FIG. 5, while straight rails (72-74) extending along two axes are provided in FIG. 7 to move the sample probes in a plane.

In FIG. 8, the interference between the sample probe heads 75 and 76 is avoided by using two pairs of straight rails intersecting at an obtuse angle instead of avoiding the interference (contact) between the two sample probes by using the curved rail 101 in FIG. 5 and by using two pairs of straight rails intersecting at a right angle in FIG. 7.

When sucking of the required amount of the sample from the relevant sample container is completed, the rack 11 is conveyed by the conveyer mechanism 12 such that the next sample container comes to the sample suction position.

Unlike FIGS. 5, 7 and 8 in which the sample probe is provided on the dispensing mechanism moving along one or more rails, the sampling position can also be adjusted by providing a dispensing arm on the moving mechanism and controlling the dispensing arm to rotate or translate as desired.

A certain amount of reagent is pipetted from the reagent container 40 placed on the reagent disk 41 or 42 into the reaction cuvette by the reagent probe 20, 21, 22 or 23. A mixture of the sample and the reagent is stirred by the mixing unit 30 or 31 to develop a reaction for a predetermined time, and is subjected to measurement by the optical detector 51. A measured result is outputted to a control computer (not shown). If there still remains a requested measurement item, the above-described sampling steps are repeated. More specifically, while the sample probe 15 discharges the sucked sample into the reaction cuvette 35, the sample probe 16 sucks the sample from the sample container 10. Then, at the time when the measurement items required for the same sample container 10 are all completed, the sample probe 15 or 16 sucks the sample from the next sample container 10. Such a sampling process by the sample probes 15, 16 is repeated until sampling for all the measurement items set for all of the sample containers 10 loaded on the rack 11 is completed.

The sample probes 15, 16 and the reagent probes 20, 21, 22 and 23 can be operated in any desired combinations. Therefore, even when one of the sample probes 15, 16 has failed to continue the operation because of any abnormality, the analysis can be continued for all the reagent items arranged on the analyzer by using the other sample probe.

Also, when it is already known that one of the sample probes 15 and 16 is in an abnormal state, the analysis can be started by setting only the sample probe free from abnormality to be effective.

Furthermore, the clogging detection function of one of the sample probes 15, 16 determines that any sample clogging factor exists in the sample container 10 or that the sample is exhausted, the sample probe for which the clogging has been detected is moved to the washing port 54 for washing of its flow passage, whereas the other sample probe can be controlled so as to stop the sucking operation from the relevant sample container and to make a shift to the sucking operation from the next sample container 10 on the rack 11. Even in the case where the status judgment shows that the sample container 10 on the rack 11 cannot be moved to the sample suction position in time, the analyzing operation can be continued without causing useless vacant cycles because the sample probe 15 or 16 is able to suck the sample from any desired one of plural positions.

Particularly, when the amount of the sample in the sample container is very small such as the case of a sample taken from an infant, it is possible to reduce the amount of a dummy which is required in the sampling operation to prevent thinning of the sample in the sample probe and is discarded into a washing tank without being discharged into the reaction cuvette 35, by using only one of the sample probes 15 and 16.

As described above, the present invention can provide an automatic analyzer, in which an analyzer includes a plurality of sample dispensing mechanisms capable of operating independently of each other, and which has a high processing capability per hour and a high value added.

What is claimed is:

1. An automatic analyzer comprising:
    an optical detector for analyzing a sample in a reaction cuvette;
    a plurality of said sample probes, each said sample probe including a sample probe head having a sample nozzle for dispensing a sample, each said sample probe including a liquid level detecting means detecting a surface level of a liquid, each of said sample probes moving from a sample suction position to a sample discharging position along a different moving path;
    a plurality of reaction cuvettes into which samples are dispensed by said sample probes and in which a reaction takes place followed by analysis with said optical detector;
    a plurality of washing ports for washing each of said sample probes, each of said washing ports being arranged along each of said moving paths,
    a controller for controlling said sample probes to reciprocally move between a single sample container containing sample at said sample suction position and a reaction cuvette at said sample discharge position to receive said sample alternately so as to prevent said sample probes from colliding with each other; and
    said controller controls one of said sample probes to detect a surface level of said sample in one said sample container, and said controller controls the sample dispensing operations of the other said sample probe on the basis of the information regarding said surface level of said sample in said one sample container.

2. An automatic analyzer according to claim 1, wherein said controller stops use of any of said sample probes and controls carrying out sampling by another one of said sampling probes.

3. An automatic analyzer according to claim 1, wherein said controller further changes from one said sample container from which a sample is to be aspirated to another said sample container that is different from said one sample container, and controls said another said sample probe to aspirate a sample from said another sample container.

* * * * *